(12) United States Patent
Lund et al.

(10) Patent No.: US 6,362,309 B1
(45) Date of Patent: Mar. 26, 2002

(54) POLYMERIZATION CATALYST LIGANDS, CATALYTIC METAL COMPLEXES AND COMPOSITIONS AND PROCESSES USING AND METHOD OF MAKING SAME

(75) Inventors: Cheryl Lund, Milpitas; Keith Anthony Hall, San Jose; Thomas Boussie, Menlo Park; Vince Murphy, Cupertino, all of CA (US); Gregory Hillhouse, Chicago, IL (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/540,480

(22) Filed: Mar. 31, 2000

Related U.S. Application Data

(60) Provisional application No. 60/127,435, filed on Apr. 1, 1999.

(51) Int. Cl.$^7$ ............................................... C08G 75/00
(52) U.S. Cl. ........................ 528/373; 528/384; 528/394; 528/398; 528/422; 528/487; 502/155; 502/168; 502/200; 502/208; 502/216
(58) Field of Search ................................ 528/373, 487, 528/384, 394; 502/155, 168, 200, 208, 216

(56) References Cited

U.S. PATENT DOCUMENTS 4,716,205 A    12/1987   Klabunde .................... 526/115

FOREIGN PATENT DOCUMENTS

| EP | 0 343 734 | 5/1989 | ............ B01J/31/22 |
| WO | WO 98/00398 | 1/1998 | ......... C07D/207/00 |
| WO | Wo 98/30609 | 7/1998 | ............ C08F/10/00 |

*Primary Examiner*—Duc Truong

(57) ABSTRACT

New compositions, metal-ligand complexes and arrays are disclosed that catalyze the polymerization of monomers into polymers.

22 Claims, No Drawings

POLYMERIZATION CATALYST LIGANDS, CATALYTIC METAL COMPLEXES AND COMPOSITIONS AND PROCESSES USING AND METHOD OF MAKING SAME

This application claims priority from U.S. Provisional application Ser. No. 06/127,435, filed Apr. 1, 1999

FIELD OF THE INVENTION

The present invention relates to new compositions that provide useful catalysts for polymerizations.

BACKGROUND OF THE INVENTION

Ancillary (or spectator) ligand-metal coordination complexes (e.g., organometallic complexes) and compositions are useful as catalysts, additives, stoichiometric reagents, monomers, solid state precursors, therapeutic reagents and drugs. Ancillary ligand-metal coordination complexes of this type can be prepared by combining an ancillary ligand with a suitable metal compound or metal precursor in a suitable solvent at a suitable temperature. The ancillary ligand contains functional groups that bind to the metal center(s), remain associated with the metal center(s), and therefore provide an opportunity to modify the steric, electronic and chemical properties of the active metal center(s) of the complex.

Certain known ancillary ligand-metal complexes and compositions are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, dimerization, trimerization, oligomerization, Diels-Alder reactions and other transformations.

One example of the use of these types of ancillary ligand-metal complexes and compositions is in the field of polymerization catalysis. In connection with single site catalysis, the ancillary ligand offers opportunities to modify the electronic and/or steric environment surrounding an active metal center. This allows the ancillary ligand to create possibly different polymers. Certain polymerization catalysts are known. See U.S. Pat. No. 4,336,360, EP Application No. 0 343 734 and Japanese Kokai Patent 09-255713, each of which is incorporated herein by reference. Likewise EP 343,734 discloses catalysts compositions for use in producing polyketone polymers, preferably polymers of carbon monoxide. The catalysts compositions are based upon a palladium compound, an anion of an acid having a pKa less than 2 and a compound represented by the formula $R^1R^2M^1—R—M^2—R^3$, where $R^1$ and $R^2$ are aryl groups, $M^1$ is P or As, $M^2$ is S or Se, $R^3$ is a hydrocarbyl group and R is a bridging group having at least two carbons.

It is always a desire to discover new catalysts that will catalyze or assist in catalysis of reactions differently from known systems. This invention provides new catalyst compositions that may catalyze polymerization reactions differently, including more efficiently and selectively than known systems.

SUMMARY OF THE INVENTION

The invention disclosed herein is a new catalyst comprising metal-ligand complexes or compositions of metal precursors and ligands that catalyze polymerization and copolymerization reactions, particularly with monomers that are olefins, diolefins or otherwise acetylenically unsaturated. These compositions may also polymerize monomers that have polar functionalities in homopolymerizations or copolymerizations. The new catalyst compositions are prepared by combining a suitable ligand with a suitable metal precursor and, optionally, a suitable activator. The ligands of the composition are characterized by the general formula:

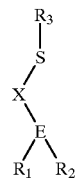

wherein each $R^1$, $R^2$, and $R^3$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure and/or $R^1$ or $R^2$ is joined together with X in a ring structure; also optionally, $R^3$ and X are joined in a ring structure; E is selected from the group consisting of nitrogen, phosphorus, arsenic and antimony (provided however that when E=N, X is not a benzylic group bound to N through the $CH_2$ of the benzylic group); and X is a covalent bridging moiety. Suitable metal precursors are characterized by the formula: $M(L)_n$ where L represents any neutral or charged ligand capable of stabilizing the metal precursor, M represents any transition metal and n is a number from 0–6, provided however that when E=P and $R^3$=H, then X cannot be $R^1R^2C—CR^3R^4$ or R1C=CR2, where $R^1$—$R^4$ are as defined above. Suitable activators are known to those skilled in the art.

For catalysis, the ligands can be included in a composition including a suitable metal, where the said composition has catalytic properties. Also, the ligands can be coordinated with a metal precursor to form metal-ligand complexes, which may be catalysts. Depending on the groups chosen for X, E, $R^1$, $R^2$, and $R^3$ in the ligand (e.g., prior to reaction with the metal precursor), the metal-ligand complexes can be characterized by one of many different general formulas depending on how the ligand attaches to or coordinates with the metal.

Thus, in another aspect of the invention, a polymerization process is disclosed for monomers. The polymerization process involves contacting one or more monomers to the catalyst compositions or to the coordination complexes of this invention under polymerization conditions. The catalyst compositions or the coordination complexes may be active catalysts themselves or make be activated with a known activating technique or compound. The polymerization process can be continuous, batch or semi-batch and can be homogeneous or heterogeneous.

Further aspects of this invention will be evident to those of skill in the art upon review of this specification.

DETAILED DESCRIPTION OF THE INVENTION

The inventions disclosed herein are metal complexes and compositions, which are useful as catalysts for chemical reactions, especially polymerization reactions.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom to any carbon of the alkyl is replaced by another group such as a halogen, aryl, substituted aryl, cycloalkyl, substituted cycloalkyl, and combinations thereof Suitable substituted alkyls include, for example, benzyl, trifluoromethyl and the like.

The term "heteroalkyl" refers to an alkyl as described above in which one or more hydrogen atoms to any carbon of the alkyl is replaced by a heteroatom selected from the group consisting of N, O, P, B, S, Si, Sb, Al, Sn, As, Se and Ge. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholinyl and the like.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and both saturated and unsaturated cyclic hydrocarbons which are fused to the aromatic ring(s), linked covalently or linked to a common group such as a methylene or ethylene moiety. The common linking group may also be a carbonyl as in benzophenone or oxygen as in diphenylether or nitrogen in diphenylamine.

The term "heteroaryl" as used herein refers to aromatic rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Substituted heteroaryl" refers to heteroaryl as just described including in which one or more hydrogen atoms to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the $-OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the —SiZ¹Z²Z³ radical, where each of Z¹, Z², and Z³ is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the —BZ¹Z² group, where each of Z¹ and Z² is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group —PZ¹Z², where each of Z¹ and Z² is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

The term "amino" is used herein to refer to the group —NZ¹Z², where each of Z¹ and Z² is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "thio" is used herein to refer to the group —SZ¹, where Z¹ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group —SeZ¹, where Z¹ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylenyl, oxazolinyl, cyclohexenyl, acetyl and the like.

Suitable ligands useful in this invention can be characterized by the general formula:

wherein each $R^1$, $R^2$, and $R^3$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure and/or $R^1$ or $R^2$ is joined together with X in a ring structure; also optionally, $R^3$ and X are joined in a ring structure; E is selected from the group consisting of nitrogen, phosphorus, arsenic and antimony (provided however that when E=N, X is not a benzylic group bound to N through the $CH_2$ of the benzylic group); and X is a covalent bridging moiety, provided however that when E=P and $R^3$=H, then X cannot be $R^1R^2C$—$CR^3R^4$ or $R1C$=$CR2$, where $R^1$—$R^4$ are as defined above.

In more specific embodiments, $R^1$ and $R^2$ and $R^3$ are independently selected from a group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl and silyl. Specific examples of $R^1$ and $R^2$ and $R^3$ are hydrogen, methyl, ethyl, propyl, butyl, cyclopentyl, cylcohexyl, cyclooctyl, phenyl, mesityl, 2,6-diisopropylphenyl, naphthyl, benzyl, trimethylsilyl, and the like. In those embodiments where $R^1$ and $R^2$ and joined together in a ring structure, the ring (including $R^1$, $R^2$ and E) has from 3 to 30 non-hydrogen atoms as part of the backbone of the ring. Specific examples of $R^1$ and $R^2$ together are ethylene (giving a 3-member ring), propylene (giving a 4-membered ring), butylene (giving a 5-membered ring), 3-oxopentylene (giving a 6-membered ring) and the like. In those embodiments where $R^1$ or $R^2$ is joined together with X in a ring structure, the ring (including $R^1$ or $R^2$ and X) has from 3 to 30 non-hydrogen atoms as part of the backbone of the ring. Specific examples of $R^1$ or $R^2$ with X together are ethylene (giving a 3-member ring), propylene (giving a 4-membered ring), butylene (giving a 5-membered ring), 3-oxopentylene (giving a 6-membered ring) and the like. In those embodiments where ether $R^3$ is joined together with X in a ring structure, the ring (including $R^3$ and X) has from 3 to 30 non-hydrogen atoms as part of the backbone of the ring. Specific examples of $R^3$ and X together are ethylene (giving a 3-member ring), propylene (giving a 4-membered ring), butylene (giving a 5-membered ring), 3-oxopentylene (giving a 6-membered ring) and the like.

In a preferred embodiment, $R^1$ and $R^2$ and $R^3$ are substituted or unsubstituted aryl groups, substituted or unsubstituted alkyl groups or substituted or unsubstituted cyclohexyl groups. If $R^1$, $R^2$, $R^3$, are substituted phenyls, there may be 1, 2, 3, 4 or 5 substituents attached to carbon atoms in the phenyl ring. Each of these substituents may be independently selected from the group consisting of alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. More preferably, there are 1, 2 or 3 substituents on the substituted phenyl and the substituents are selected from the group consisting of chloro, fluoro, iodo, bromo, trifluoromethyl, methoxy, ethoxy, phenoxy, nitro, methyl, ethyl, propyl, isopropyl, butyl, tertiarybutyl, cyclopentyl, cylcohexyl, cyclooctyl, phenyl, naphthyl, benzyl, trimethylsilyl and isomers thereof.

More specifically X is a bridging group comprising an alkyl, substituted alkyl, heteroalkyl, substituted heteroalkyl, aryl, or substituted aryl group. X may contain functional groups that may additionally bind to the metal.

Chiral ligands of the formulae described above are especially useful in this invention.

The ligands of this invention may be synthesized using known procedures. See, for example, Advanced Organic Chemistry, March, Wiley, N.Y. 1992 (4$^{th}$ Ed.). Once the desired ligand is formed, it may be combined with a metal atom, ion, compound or other metal precursor compound. In those embodiments where one of more of $R^1$ or $R^2$ or $R^3$ is a hydrogen atom, the ligand may be deprotonated prior to combining the ligand with the metal precursor compound. In many applications, the ligands of this invention will be combined with such a metal compound or precursor and the product of such combination is not determined, if a product forms. For example, the ligand may be added to a reaction vessel at the same time as the metal or metal precursor compound along with the reactants. The metal precursor compounds may be characterized by the general formula M(L)$_n$ where M is a metal selected from the group consisting of Groups 3, 4, 5, 6, 7, 8, 9, 10, 11 and 12 of the Periodic Table of Elements and n is an integer that depends on the metal and the ligands L chosen for the metal, e.g., such as whether the ligands L are neutral or charged. In more specific embodiments, M is selected from the group consisting of Ti, Zr, Hf, V, Ta, Nb, Cr, W, Mo, Ru, Os, Co, Rh, Ir, Ni, Pd, Fe, Mn, Re, Cu, Zn and Pt. L is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, carboxylates, acetylacetates, and combinations thereof. n is 0, 1, 2, 3, 4, 5 or 6. When n is greater than 1, then each L is independently selected from the ligands above. Specific examples of suitable metal precursor compounds include Ti(CH$_2$Ph)$_4$, Zr(CH$_2$Ph)$_4$, Hf(CH$_2$Ph)$_4$, V(mesityl)$_3$(THF), Ta(CH$_3$)$_3$(Cl)$_2$, Nb(CH$_3$)$_3$(Cl)$_2$, Ta(NMe$_2$)$_3$(Cl)$_2$, Cr(CHTMS$_2$)$_3$, Cr(mesityl)$_2$(THF), Cr(mesityl)$_2$(THF)$_3$, [Fe(mesityl)$_2$]$_2$, [Co(mesityl)$_2$]$_2$, Co(mesityl)$_3$Li(THF)$_4$, [Mn(mesityl)$_2$]$_3$, Cr(mesityl)$_3$, Sc(CH(SiMe$_3$)$_2$)$_3$, Y(CH(SiMe$_3$)$_2$)$_3$, Ln(CH(SiMe$_3$)$_2$)$_3$, Sc(O(2,6-(Bu$^t$)$_2$C$_6$H$_3$))$_3$, Y(O(2,6-(tBu)$_2$C$_6$H$_3$))$_3$, Ln(O(2,6-(Bu$^t$)$_2$C$_6$H$_{3)})_3$, Sc(O(2,6-(Bu$^t$)$_2$-4-Me-C$_6$H$_3$))$_3$, Y(O(2,6-(tBu)$_2$-4-Me-C$_6$H$_3$))$_3$, Ln(O(2,6-(Bu$^t$)$_2$-4-Me-C$_6$H$_3$))$_3$, Sc(N(SiMe$_3$)$_2$)$_3$ Y(N(SiMe$_3$)$_2$)$_3$, Ln(N(SiMe$_3$)$_2$)$_3$, (where Ln =La, Ce, Pr, Nd, Sm, Eu, Gd, Tb, Dy, Ho, Er, Tm, Yb, and Lu), Ni(acac)$_2$, Pd(acac)$_2$, Co(acac)$_3$, Fe(acac)$_3$, Fe(acac)$_2$, Mn(acac)$_2$, Cr(acac)$_2$, Cr(acac)$_3$, V(acac)$_3$, V(O)(acac)$_3$, Ni(TFA)$_2$, Fe(TFA)$_2$, Fe(TFA)$_3$, Co(TFA)$_2$, Mn(TFA)$_2$, [Cr(TFA)$_2$]$_2$, Cr(TFA)$_3$, V(TFA)$_3$, CrCl$_3$(THF)$_3$, VCl$_3$(THF)$_3$, (COD)PdMeCl, [(cyclooctene)PdMeCl]$_2$, (COD)PdMeOTf, [(allyl)PdCl]$_2$, [(allyl)NiCl]$_2$, [(CH$_3$O$_2$CC$_3$H$_4$)NiBr]$_2$, [(allyl)NiTFA]$_2$, (p-cymene)Ru(TFA)$_2$(CH$_3$CN), (p-cymene)Ru(mesityl)(TFA), (PPh$_3$)$_4$ RuH$_2$, (PPh$_3$)$_2$Ni(Ph)Cl, (PPh$_3$)$_4$Ni, (COD)$_2$Ni, (py)$_2$Ni(CH$_2$SiMe$_3$)$_2$, Fe(C(SiMe$_3$)$_3$)$_2$, Co(C(SiMe$_3$)$_3$)$_2$, Mn(C(SiMe$_3$)$_3$)$_2$, Ti(CH$_2$CMe$_3$)$_4$, Zr(CH$_2$CMe$_3$)$_4$, Hf(CH$_2$CMe$_3$)$_4$, TiCl$_4$, Ti(NMe$_2$)$_4$, Zr(NMe$_2$)$_4$, Hf(NMe$_2$)$_4$, Zr(NEt$_2$)$_4$, Ti(NMe$_2$)$_2$Cl$_2$, Zr(N(SiMe$_3$)$_2$)$_2$Cl$_2$, Hf(N(SiMe$_3$)$_2$)$_2$Cl$_2$, Zr(TFA)$_4$, Hf(TFA)$_4$, Ti(TFA)$_2$Cl$_2$, TiCl$_3$(THF)$_3$, V(CH(SiMe$_3$)$_2$)$_3$(THF), V(O-2,6-Pr$^i$—C$_6$H$_3$)$_4$Li(THF), Ta(NMe$_2$)$_5$, (TMEDA)NiMe$_2$, (TMEDA)PdMe$_2$, Ta(CH$_2$CMe$_3$)$_2$Cl$_3$, TaPh$_5$, Co(PPh$_3$)$_3$CH$_3$, [Co(PPh$_3$)$_3$H]$_2$N$_2$, and [Ni(PCy$_3$)$_2$]$_2$ N$_2$ and the like. (TFA=trifluoroacetate; COD=1,5-cyclooctadiene; TMEDA=tetramethylethylenediamine; OTf=triflate; THF=tetrahydrofuran; Pr$^i$=isopropyl; py=pyridine; acac=acetylacetanoate; mesityl=2,4,6-Me$_3$C$_6$H$_2$-, Bu$^t$=tertiary butyl.)In this context, the ligand to metal precursor compound ratio is in the range of about 0.01:1 to about 100:1, more preferably in the range of about 0.5:1 to about 20:1.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst. Depending on the substituents chosen for the ligand prior to reaction with the metal precursor compound, the metal complexes may be characterized by any of the following general formulae:

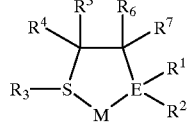

II

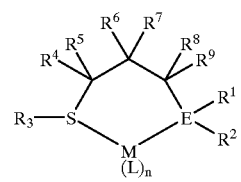

III

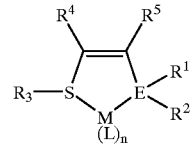

IV

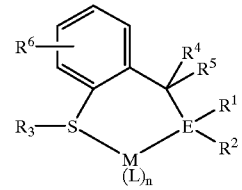

V

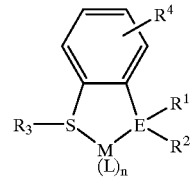

VI

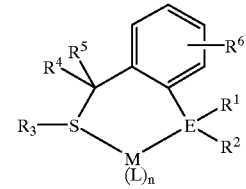

VII

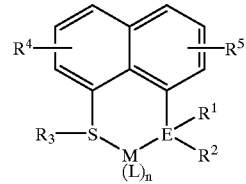

VIII

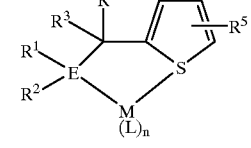

IX wherein each $R^1$, $R^2$, $R^3$, $R^4$, $R^5$, $R^6$, $R^7$, $R^8$, and $R^9$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; E is selected from the group consisting of nitrogen, phosphorus, arsenic and antimony (provided however that when E=N, X is not a benzylic group bound to N through the CH$_2$ of the benzylic group); and X is a covalent bridging moiety, as defined above provided however that when E=P and R$^3$=H, then X cannot be R$^1$R$^2$C—CR$^3$R$^4$ or R1C=CR2, where R$^1$—R$^4$ are as defined above. M is a transition metal selected from the group consisting of Groups 3, 4, 5, 6, 7, 8, 9, 10, 11 and 12 of the Periodic Table of Elements. Selection of the metal is most preferably dependent on the ligand structure. L is independently each occurrence, a neutral and/or charged ligand. Generally, L is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, carboxylates, acetylacetates, and combinations thereof; and n is 0, 1, 2, 3, 4, 5, or 6, when n is greater than 1, each L is independently selected from the ligands above.

Dimers, trimers or higher orders of the above are also useful to the invention. Additionally, examples where two or more metal atoms are bridged by one or more ligands are useful in the invention. Furthermore, two or more ligands may coordinate with a single metal atom. The nature of the metal complex or complexes formed most likely depends on the chemistry of the ligand and the metal precursor and the method of combining the ligand and metal precursor, such that a distribution of metal complexes may form with the number of ligands bound to the metal being greater than or less then the number of equivalents of ligands added relative to an equivalent of the metal precursor.

Within each of these formulae, specific examples include, but are not limited to:

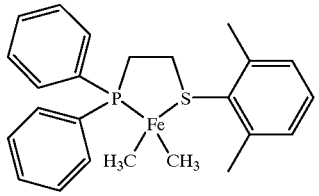

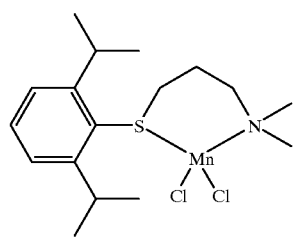

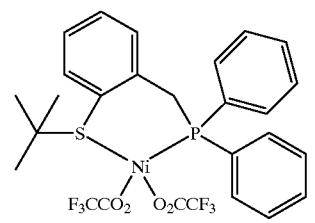

-continued

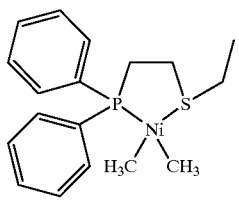

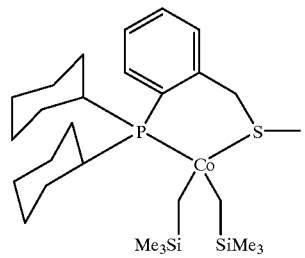

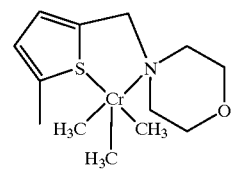

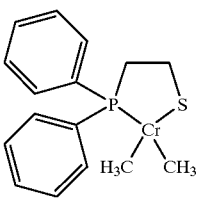

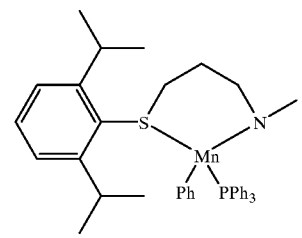

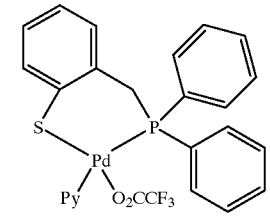

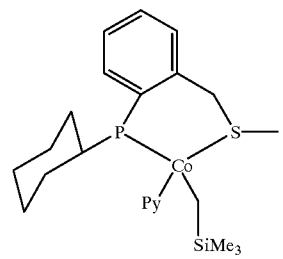

-continued

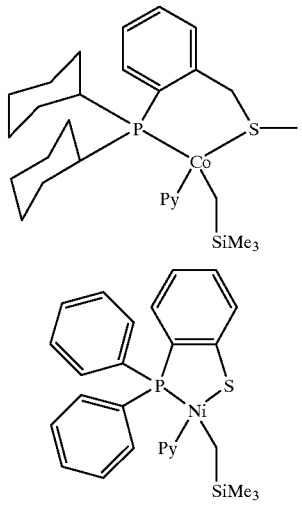

Dimers, trimers or higher orders of the above are also useful to the invention. Additionally, examples where two or more metal atoms are bridged by one or more ligands are useful in the invention. Furthermore, two or more ligands may coordinate with a single metal atom. The nature of the metal complex or complexes formed most likely depends on the chemistry of the ligand and the metal precursor and the method of combining the ligand and metal precursor, such that a distribution of metal complexes may form with the number of ligands bound to the metal being greater than or less then the number of equivalents of ligands added relative to an equivalent of the metal precursor.

The ligands may be supported, with or without the metal coordinated, on an organic or inorganic support. Suitable supports include silicas, aluminas, zeolites, polyethyleneglycols, polystyrenes, polyesters, polyamides, peptides and the like. Similarly, the metal may be supported with or without the ligand, on similar supports known to those of skill in the art.

Polymerization catalysis with the compositions and metal complexes of this invention is a particularly effective process. In particular, the complexes and compositions of this invention are active catalysts also for the polymerization of olefins, possibly in combination with an activator or activating technique. When an activator or activating technique is used, those of skill in the art may use alumoxanes, strong Lewis acids, compatible non-interfering activators and combinations of the foregoing. The foregoing activators have been taught for use with different compositions or metal complexes in the following references, which are hereby incorporated by reference in their entirety: U.S. Pat. Nos. 5,599,761, 5,616,664, 5,453,410, 5,153,157, 5,064,802, and EP-A-277,004. Preferred activators include methylalumoxane, trimethylaluminum, $AgBF_4$, $AgBPh_4$, $NaBAr'_4$, $H(OEt_2)_2BAr'_4$ and the like (where Ar' is a substituted aromatic, like perfluorophenyl or $3,5-(CF_3)_2(C_6H_3)$). Ratios of neutral complex to activator are on the order of 1 to 1000 to 1000 to 1. A scavenger can also be used with this invention. Scavengers useful herein include the metal complexes, alumoxanes, aluminum alkyls and the like. Other additives that are standard for polymerization reactions can be used.

Suitable ion forming compounds useful as an activator in one embodiment of the present invention comprise a cation which is a Bronsted acid capable of donating a proton, and an inert, compatible, non-interfering, anion, $A^-$. Preferred anions are those containing a single coordination complex comprising a charge-bearing metal or metalloid core. Mechanistically, said anion should be sufficiently labile to be displaced by olefinic, diolefinic and acetylenically unsaturated compounds or other neutral Lewis bases such as ethers or nitrites. Suitable metals include, but are not limited to, aluminum, gold and platinum. Suitable metalloids include, but are not limited to, boron, phosphorus, and silicon. Compounds containing anions that comprise coordination complexes containing a single metal or metalloid atom are, of course, well known and many, particularly such compounds containing a single boron atom in the anion portion, are available commercially.

Preferably such activators may be represented by the following general formula:

$$(L^*-H)_d^+(A^{d-})$$

wherein, $L^*$ is a neutral Lewis base; $(L^*-H)^+$ is a Bronsted acid; $A^{d-}$ is a non-interfering, compatible anion having a charge of d-, and d is an integer from 1 to 3. More preferably $A^{d-}$ corresponds to the formula: $[M'^{3+} Q_h]^{d-}$ wherein h is an integer from 4 to 6; h−3=d; M' is an element selected from Group 13 of the Periodic Table of the Elements; and Q is independently selected from the group consisting of hydride, dialkylamido, halide, alkoxide, aryloxide, hydrocarbyl, and substituted-hydrocarbyl radicals (including halosubstituted hydrocarbyl, such as perhalogenated hydrocarbyl radicals), said Q having up to 20 carbons. In a more preferred embodiment, d is one, i.e., the counter ion has a single negative charge and corresponds to the formula $A^-$.

Activators comprising boron or aluminum which are particularly useful in the preparation of catalysts of this invention may be represented by the following general formula:

$$[L^*-H]^+[JQ_4]^-$$

wherein: $L^*$ is as previously defined; J is boron or aluminum; and Q is a fluorinated $C_{1-20}$ hydrocarbyl group. Most preferably, Q is independently selected from the group selected from the group consisting of fluorinated aryl group, especially, a pentafluorophenyl group (i.e., a $C_6F_5$ group) or a $3,5-bis(CF_3)_2C_6H_3$ group. Illustrative, but not limiting, examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethylanilinium tetra-(3,5-bis (trifluoromethyl)phenyl)borate, N,N-dimethyl-(2,4,6-trimethylanilinium) tetraphenylborate, trimethylammonium tetrakis(pentafluorophenyl) borate, triethylammonium tetrakis(pentafluorophenyl) borate, tripropylammonium tetrakis(pentafluorophenyl)borate, tri(n-butyl)ammonium tetrakis(pentafluorophenyl)borate, tri(secbutyl)ammonium tetrakis(pentafluorophenyl)borate, N,N-dimethylanilinium tetrakis(pentafluorophenyl)borate, N,N-diethylanilinium tetrakis(pentafluorophenyl) borate, N,N-dimethyl-(2,4,6-trimethylanilinium) tetrakis(pentafluorophenyl) borate, trimethylammonium tetrakis-(2,3,4,6-tetrafluorophenylborate and N,N-dimethylanilinium tetrakis-(2,3,4,6-tetrafluorophenyl) borate; dialkyl ammonium salts such as: di-(i-propyl)ammonium tetrakis(pentafluorophenyl) borate, and dicyclohexylammonium tetrakis(pentafluorophenyl)

borate; and tri-substituted phosphonium salts such as: triphenylphospnonium tetrakis(pentafluorophenyl) borate, tri(o-tolyl)phosphonium tetrakis(pentafluorophenyl) borate, and tri(2,6-dimethylphenyl)phosphonium tetrakis(pentafluorophenyl) borate; and N,N-dimethylanilinium tetrakis(3,5-bis(trifluoromethyl)phenyl)borate. Preferred [L*–H]+ cations are N,N-dimethylanilinium and tributylammonium. Preferred anions are tetrakis(3,5-bis(trifluoromethyl)phenyl)borate and tetrakis(pentafluorophenyl)borate. In some embodiments, the most preferred activator is $PbNMe_2H^+B(C_6F_5)_4^-$.

Other suitable ion forming activators comprise a salt of a cationic oxidizing agent and a non-interfering, compatible anion represented by the formula:

$$(Ox^{e+})_d(A^{d-})_e$$

wherein: $Ox^{e+}$ is a cationic oxidizing agent having a charge of e+; e is an integer from 1 to 3; and $A^{d-}$, and d are as previously defined. Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion or silyl cation and a non-interfering, compatible anion represented by the formula:

$$C^+A^-$$

wherein: $C^+$ is a $C_{1-100}$ carbenium ion or silyl cation; and $A^-$ is as previously defined. A preferred carbenium ion is the trityl cation, i.e. triphenylcarbenium. The silyl cation may be characterized by the formula $Z^1Z^2Z^3Si^+$ cation, where each of $Z^1$ $Z^2$, and $Z^3$ is independently selected from the group consisting of hydrogen, alkyl, substituted alkyl, cycloalkyl, heterocycloalkyl, heterocyclic, aryl, substituted aryl, heteroaryl, substituted heteroaryl and combinations thereof. In some embodiments, a most preferred activator is $Ph_3C^+B(C_6F_5)_4^-$.

In addition, suitable activators include Lewis acids, such as those selected from the group consisting of tris(aryl)boranes, tris(substituted aryl)boranes, tris(aryl)alanes, tris(substituted aryl)alanes, including activators such as tris(pentafluorophenyl)borane. Other useful ion forming Lewis acids include those having two or more Lewis acidic sites, such as those described in WO 99/06413 or Piers, et al. "New Bifunctional Perfluoroaryl Boranes: Synthesis and Reactivity of the ortho-Phenylene-Bridged Diboranes 1,2-[B(C_6F_5)_2]_2C_6X_4 (X=H, F)", J. Am. Chem. Soc., 1999, 121, 3244–3245, both of which are incorporated herein by reference. Other useful Lewis acids will be evident to those of skill in the art. In general, the group of Lewis acid activators are within the group of ion forming activators (although exceptions to this general rule can be found) and the group tends to exclude the group 13 reagents listed below. Combinations of ion forming activators may be used.

Other general activators or compounds useful in a polymerization reaction may be used. These compounds may be activators in some contexts, but may also serve other functions in the polymerization system, such as alkylating a metal center or scavenging impurities. These compounds are within the general definition of "activator," but are not considered herein to be ion forming activators. These compounds include a group 13 reagent that may be characterized by the formula $G^{13}R'_{3-p}D_p$ where $G^{13}$ is selected from the group consisting of Al, B, Ga, In and combinations thereof, p is 0, 1 or 2, each R' is independently selected from the group consisting of alkyl, substituted alkyl, cycloalkyl, heterocycloalkyl, heterocyclic and combinations thereof, and each D is independently selected from the group consisting of halide, hydride, alkoxy, aryloxy, amino, thio, phosphino and combinations thereof. In other embodiments, the group 13 activator is an oligomeric or polymeric alumoxane compound, such as methylalumoxane and the known modifications thereof. In other embodiments, a divalent metal reagent may be used that is defined by the general formula $M'R'_{2-p'}D_{p'}$ and p' is 0 or 1 in this embodiment and R' and D are as defined above. M' is the metal and is selected from the group consisting of Mg, Ca, Sr, Ba, Zn, Cd and combinations thereof In still other embodiments, an alkali metal reagent may be used that is defined by the general formula M"R' and in this embodiment R' is as defined above. M" is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula $SiR'_{4-q}D_q$ where R' is defined as above, q is 1, 2, 3 or 4 and D is as defined above, with the proviso that there is at least one D that is a hydride.

The molar ratio of metal precursor:activator employed preferably ranges from 1:10,000 to 100:1, more preferably from 1:5000 to 10:1, most preferably from 1:10 to 1:1. In a preferred embodiment of the invention mixtures of the above compounds are used, particularly a combination of a group 13 reagent and an ionic activator (i.e., those with a positive and negative charge). The molar ratio of group 13 reagent to ionic activator is preferably from 1:10,000 to 1000:1, more preferably from 1:5000 to 100:1, most preferably from 1:100 to 100:1. In a preferred embodiment, the ion forming activators are combined with a tri-alkyl aluminum, specifically trimethylaluminum, triethylaluminum, or triisobutylaluminum or with a di-alkyl aluminum hydride such as di-isobutyl aluminum hydride.

The compositions and catalysts herein may be used to polymerize ethylenically or acetylenically unsaturated monomers having from 2 to 20 carbon atoms either alone or in combination The compounds and catalysts of this invention also usefully polymerize functionalized monomers, such as acetates and acrylates. Monomers olefins, diolefins and acetylenically unsaturated monomers, including $C_2$ to $C_{20}$ α-olefins such as ethylene, propylene, 1-butene, 1-hexene, 1-octene, 4-methyl-1-pentene, 1-norbornene, styrene, and mixtures thereof; additionally, 1,1-disubstituted olefins, such as isobutylene, either alone or with other monomers such as ethylene or $C_3$ to $C_{20}$ α-olefins and/or diolefins. These definitions are intended to include cyclic olefins. Diolefins generally comprise 1,3-dienes such as (butadiene), substituted 1,3-dienes (such as isoprene) and other substituted 1,3-dienes, with the term substituted referring to the same types of substituents referred to above in the definition section. Diolefins also comprises 1,5-dienes and other non-conjugated dienes. The use of diolefins in this invention is typically in conjunction with another monomer that is not a diolefin. The styrene monomers may be unsubstituted or substituted at one or more positions on the aryl ring. One class of functionalized monomers can be characterized by the general formula $H_2C=CH—FG$, where FG is the functional group that contains at least one heteroatom (using the previous definition) or halogen (e.g., Cl, F, Br, etc.). Functionalized monomers include $C_1$–$C_{20}$ acrylates, $C_1$–$C_{20}$ methacrylates, acrylic acid, methacrylic acid, maleic anhydride, vinyl acetate, acrylonitrile, acrylamide, vinyl ethers, vinyl chloride, and mixtures thereof. The compositions of this invention may also be used to copolymerize two or more of the monomers described herein. Novel polymers, copolymers or interpolymers may be formed having unique physical and/or melt flow properties. Such novel polymers can be employed alone or with other polymers in a blend to form products that may be molded, cast, extruded or spun. End uses for the polymers made with the catalysts of this invention include films for packaging, trash bags, bottles, containers, foams, coatings, insulating devices and household items. Also, such functionalized polymers are useful as solid supports for organometallic or chemical synthesis processes.

Polymerization can be carried out in the Ziegler-Natta or Kaminsky-Sinn methodology, including temperatures of from –100° C. to 400° C. and pressures from atmospheric to 3000 atmospheres. Suspension, solution, slurry, gas phase or high-pressure polymerization processes may be employed with the catalysts and compounds of this invention. Such processes can be run in a batch, semi-batch or continuous mode. Examples of such processes are well known in the art. A support for the catalyst may be employed, which may be inorganic (such as alumina, magnesium chloride or silica) or organic (such as a polymer or cross-linked polymer). Methods for the preparation of supported catalysts are known in the art. Slurry, suspension, solution and high-pressure processes use a suitable solvent as known to those skilled in the art.

Suitable solvents for polymerization are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof, perfluorinated hydrocarbons such as perfluorinated $C_{4-10}$ alkanes, and aromatic and alkylsubstituted aromatic compounds such as benzene, toluene, and xylene. Suitable solvents also include liquid olefins which may act as monomers or comonomers including ethylene, propylene, 1-butene, butadiene, cyclopentene, 1-hexene, 1-pentene, 3-methyl-1-pentene, 4-methyl-1-pentene, 1,4-hexadiene, 1-octene, 1-decene, isobutylene, styrene, divinylbenzene, allylbenzene, vinyltoluene (including all isomers alone or in admixture), vinyl chloride, acrylonitrile, acrylates, vinyl acetate, methacrylates, 4-vinylcyclohexene, and vinylcyclohexane. Mixtures of the foregoing are also suitable.

Other additives that are useful in a polymerization reaction may be employed, such as scavengers, promoters, etc.

The ligands, metal complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. U.S. Pat. No. 5,776,359 and WO 98/03521, both of which are incorporated herein by reference, generally disclose combinatorial methods. In this regard, the metal precursors, ligands, complexes or compositions may be prepared and/or tested in rapid serial and/or parallel fashion, e.g., in an array format. When prepared in an array format, for example, the metal precursors, activators and/or ligands may take the form of an array comprising a plurality of compounds wherein each compound can be characterized by the general formula

where $R^1, R^2, R^3, X, E$ are as defined above. Typically, each member of the array will have differences so that, for example, $R^1$ in a first region of the array may be different than $R^1$ in a second region of the array. Other variables may also differ from region to region in the array. The array may also be of metal-ligand complexes or composition as discussed above; for example the members of the array may be characterized by any of the formulae I, II, III, IV, V, VI, VII, VIII or IX, discussed above. In a preferred embodiment, when E=P and $R^3$=H, then X cannot be $R^1R^2C$—$CR^3R^4$ or R1C=CR2, where $R^1$–$R^4$ are as defined above In such a combinatorial array, typically each of the plurality of compounds has a different composition or stoichiometry and, typically each composition or complex is at a selected region on a substrate such that each is isolated from the other compositions or complexes. This isolation can take many forms, typically depending on the substrate used. If a flat substrate is used, there may simply be sufficient space between regions so that there cannot be interdiffusion between compositions or complexes. As another example, the substrate can be a microtiter or similar plate having wells so that each compsition or complex is in a region separated from other compounds in other regions by a physical barrier. The array may also comprise a parallel reactor or testing chamber.

The array typically comprises at least 8 compounds, complexes or compositions each having a different chemical make-up, meaning that there is, typically, at least one different atom or bond differentiating the members in the array or different ratios of the components referred to herein (with components referring to metal precursors, activators, group 13 reagents, solvents, monomers, supports, etc.). In other embodiments, there are at least 20 compounds, complexes or compositions on or in the substrate each having a different chemical formula or ratio of components. In still other embodiments, there are at least 40 or 90 or 124 compounds, complexes or compositions on or in the substrate each having a different chemical formula or ratio of components. Because of the manner of forming combinatorial arrays, it may be that each compound, complex or composition may not be worked-up, purified or isolated, and for example, may contain reaction by-products or impurities or unreacted starting materials.

The catalytic performance of the ligands of this invention alone or in combination with a suitable metal precursor or metal-ligand coordination complexes of this invention can be tested in a combinatorial or high throughput fashion. Polymerizations can also be performed in a combinatorial fashion, see, e.g., provisional U.S. patent application Ser. Nos. 60/096,603, filed Aug. 13, 1998, Ser. No. 09/211,982, filed Dec. 14, 1998 and Ser. No. 09/239,223, filed Jan. 29, 1999, each of which is incorporated by reference herein. High throughput screening can also be performed optically and in parallel, for example, as disclosed in U.S. patent applications Ser. No. 08/947,085, filed Oct. 8, 1997, and Ser. No. 08/946,135, filed Oct. 7, 1997, each of which is incorporated by reference.

EXAMPLES

General: All reactions were performed under argon or nitrogen atmosphere in a Vacuum Atmospheres glove box. All solvents used were of the anhydrous, Sure-Seal® grade. Polymerizations were carried out in a parallel polymerization reactor, which is fully described in pending U.S. patent applications Ser. No. 09/177,170, filed Oct. 22, 1998, Ser. No. 09/211,982, filed Dec. 14, 1998 and Ser. No. 09/239,223, filed Jan. 29, 1999, each of which is incorporated herein by reference. The total volume of each polymerization reaction was 5 ml. Polymerizations were carried out under identical conditions at 25° C. at 50 psi (345 kPa) of ethylene. Synthesis of the metal-ligand compositions: In a 10 ml glass reaction tube under $N_2$ is combined 16.7 µl of a $3\times10^{-2}$ M solution ($5\times10^{-4}$ mmol) of the ligand in dichloroethane and 167 µl of a $3\times10^{-3}$ M solution ($5\times10^{-4}$ mmol) of the metal precursor in 10% diethylether/dichloroethane solution. The mixture is covered for 2 hours at room temperature, then uncovered and the solution allowed to evaporate to dryness over 12 hours. The product is then dried in vacuo for 20 minutes at 1 torr. Table 1 shows the metal-ligand combinations.

TABLE 1

| Example | Ligand | Metal Precursor |
| --- | --- | --- |
| 2 |  | $Ni(O_2CCF_3)_2$ |
| 3 | 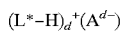 | $Cr(O_2CCF_3)_2$ |

Activation with MAO and Ethylene Polymerization. The reaction tube containing the metal-ligand composition was placed into a reactor block and charged with 4.9 mL anhydrous toluene. The reactor block was sealed and pressurized with ethylene (50 psi/345 kPa)) with mechanical stirring of the solution. After 10 minutes the reactor block was opened and a 100 µl of a 1.5 M solution (0.15 mmol, 300 eq) of MAO in toluene was added to the reaction tube and the reactor block resealed. Polymerizations were conducted in a semi-batch mode at 50 psi ethylene for 2 hours. Polyethylene polymers were obtained for all of the metal-ligand examples shown in Table 1 as determined by molecular weight measurements obtained from gel permeation chromatography.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A polymerization reaction employing a composition comprising:

(1) a compound characterized by the general formula:

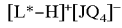

wherein each $R^1$, $R^2$, and $R^3$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure and/or $R^1$ or $R^2$ is joined together with X in a ring structure; also optionally, $R^3$ and X are joined in a ring structure; E is selected from the group consisting of nitrogen and phosphorus (provided however that when E is N, X is not a benzylic group bound to N through the $CH_2$ of the benzylic group); and X is a covalent bridging moiety;

(2) a metal precursor are characterized by the formula: $M(L)_n$; where M is a transition metal selected from the group consisting of Groups 3, 4, 5, 6, 7, 8, 9, 10, 11 and 12 of the Periodic Table of Elements; L is independently each occurrence, a ligand; and n is 0, 1, 2, 3, 4, 5 or 6;

provided however that when E is P and $R^3$ is H, then X cannot be $R^4R^5C$—$CR^6R^7$ or $R^4C$=$CR^5$, wherein $R^4$–$R^7$ are independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and, (3) optionally, at least one activator.

2. The reaction of claim 1 wherein the at least one activator is present and is selected from the group consisting of alumoxanes, Lewis acids, compatible non-interfering activators or combinations thereof.

3. The reaction of claim 1 wherein the at least one activator is present and is represented by the formula:

$$(L^*-H)_d^+(A^{d-})$$

wherein, $L^*$ is a neutral Lewis base; $(L^*-H)^+$ is a Bronsted acid; $A^{d-}$ is a non-interfering, compatible anion having a charge of d−, and d is an integer from 1 to 3.

4. The reaction of claim 3 wherein $A^{d-}$ corresponds to the formula: $[M'^{3+}Q_h]^{d-}$ wherein h is an integer from 4 to 6; h−3=d; M' is an element selected from Group 13 of the Periodic Table of the Elements; and Q is independently selected from the group consisting of hydride, dialkylamido, halide, alkoxide, aryloxide, hydrocarbyl, and substituted-hydrocarbyl radicals (including halosubstituted hydrocarbyl, such as perhalogenated hydrocarbyl radicals), said Q having up to 20 carbons.

5. The reaction of claim 1 wherein at least one activator is present and is represented by the formula:

$$[L^*-H]^+[JQ_4]^-$$

wherein: $L^*$ is a neutral Lewis base; J is boron or aluminum; and Q is a fluorinated $C_{1-20}$ hydrocarbyl group.

6. The reaction of claim 5 wherein each Q is independently selected from the group selected from the group consisting of fluorinated aryl groups.

7. The reaction of claim 1 wherein the at least one activator is present and is selected from the group consisting of tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl) ammonium tetraphenylborate, N,N-dimethylanilinium tetraphenylborate, N,N-diethylanilinium tetraphenylborate, N,N-dimethylanilinium tetra-(3,5-bis(trifluoromethyl)phenyl)borate, N,N-dimethyl-(2,4,6-trimethylanilinium) tetraphenylborate, trimethylammonium tetrakis(pentafluorophenyl) borate, triethylammonium tetrakis(pentafluorophenyl) borate, tripropylammonium tetrakis(pentafluorophenyl)borate, tri(n-butyl)ammonium tetrakis(pentafluorophenyl)borate, tri(secbutyl)ammonium tetrakis(pentafluorophenyl)borate, N,N-dimethylanilinium tetrakis(pentafluorophenyl)borate, N,N-diethylanilinium tetrakis(pentafluorophenyl) borate, N,N-dimethyl-(2,4,6-trimethylanilinium) tetrakis(pentafluorophenyl) borate, trimethylammonium tetrakis-(2,3,4,6-tetrafluorophenylborate and N,N-dimethylanilinium tetrakis-(2,3,4,6-tetrafluorophenyl) borate; di-(i-propyl) ammonium tetrakis(pentafluorophenyl) borate, dicyclohexylammonium tetrakis(pentafluorophenyl) borate; triphenylphospnonium tetrakis(pentafluorophenyl) borate, tri(o-tolyl)phosphonium tetrakis(pentafluorophenyl) borate, tri(2,6-dimethylphenyl)phosphonium tetrakis(pentafluorophenyl) borate; and N,N-dimethylanilinium tetrakis(3,5-bis(trifluoromethyl)phenyl)borate and combinations thereof.

8. The reaction of claim 1 wherein M is selected from the group consisting of Ti, Zr, Hf, V, Ta, Nb, Cr, W, Mo, Ru, Os, Co, Rh, Ir, Ni, Pd, Fe, Mn, Re, Cu, Zn and Pt.

9. The reaction of claim 1 wherein the combination of (1) and (2) forms a composition represented by the one of the following formulae:

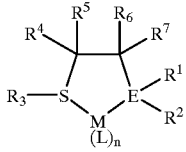

II

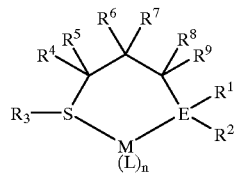

III

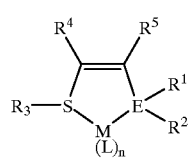

IV

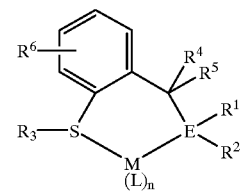

V

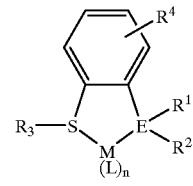

VI

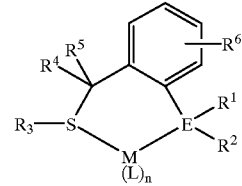

VII

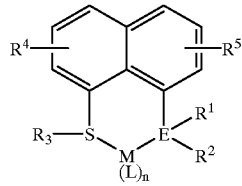

VIII

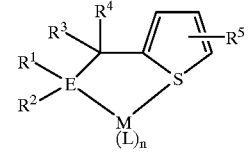

IX wherein each $R^1$, $R^2$, $R^3$, $R^4$, $R^5$, $^6$, $R^7$, $R^8$, and $R^9$, is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; E is selected from the group consisting of nitrogen, phosphorus, arsenic and antimony provided however that E=N, X is not a benzylic group bound to N through the $CH_2$ of the benzylic group); and X is a covalent bridging moiety, M is a transition metal selected from the group consisting of Groups 3, 4, 5, 6, 7, 8, 9, 10, 11 and 12 of the Periodic Table of Elements, L is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, carboxylates, acetylacetates, and combinations thereof; and n is 0, 1, 2, 3, 4, 5, or 6, provided however that when E=P and $R^3$=H, then X cannot be $R^1R^2C$—$CR^3R^4$ or $R1C$=$CR2$, where $R^1$–$R^4$ are as defined above.

10. The reaction of claim 1 wherein (1) and or (2) and or (3) is supported on a support.

11. The reaction of claim 1 wherein the at least one activator is present and is a combination of an ion forming activator and a group 13 reagent or a divalent metal reagent or alkali metal reagent.

12. A process for polymerizing an olefin, diolefin or acetylenically unsaturated compound, comprising contacting said olefin, diolefin or acetylenically unsaturated compound with a composition comprising:

(1) a compound characterized by the general formula:

wherein each $R^1$, $R^2$, and $R^3$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure and/or $R^1$ or $R^2$ is joined together with X in a ring structure; also optionally, $R^3$ and X are joined in a ring structure; E is selected from the group consisting of nitrogen and phosphorus (provided however that when E is N, X is not a benzylic group bound to N through the $CH_2$ of the benzylic group); and X is a covalent bridging moiety;

(2) a metal precursor are characterized by the formula: $M(L)_n$ where M is a transition metal selected from the group consisting of Groups 3, 4, 5, 6, 7, 8, 9, 10, 11 and 12 of the Periodic Table of Elements; L is independently each occurrence, a ligand; and n is 0, 1, 2, 3, 4, 5 or 6;

provided however that when E is P and $R^3$ is H, then X cannot be $R^4R^5C$—$CR^6R^7$ or $R^4C$=$CR^5$, wherein $R^4$–$R^7$ are independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and, (3) optionally, at least one activator.

13. The process of claim 12 wherein the olefin, diolefin or acetylenically unsaturated compound comprises one or more of $C_2$ to $C_{20}$ α-olefins, $C_1$–$C_{20}$ acrylates, and/or $C_1$–$C_{20}$ methacrylates.

14. The process of claim 12 wherein the olefin, diolefin or acetylenically unsaturated compound comprises one or more of as ethylene, propylene, 1-butene, 1-hexene, 1-octene, 4-methyl-1-pentene, 1-norbornene, styrene, isobutylene, isoprene, styrene, butadiene, acrylic acid, methacrylic acid, maleic anhydride, vinyl acetate, vinyl ethers, acrylonitrile, acrylamide, vinyl chloride and mixtures thereof.

15. The process of claim 12 wherein the olefin, diolefin or acetylenically unsaturated compound comprises ethylene.

16. The process of claim 12 wherein the polymerization is conducted in the solution phase.

17. The process of claim 12 wherein the polymerization is conducted in a high pressure polymerization process.

18. The process of claim 12 wherein (1) and or (2) and or (3) is supported on a support.

19. The process of claim 12 wherein the polymerization is conducted in the gas or slurry phase.

20. The process of claim 12 wherein the at least one activator comprises one or more of methylalumoxane trimethylammonium tetraphenylborate, triethylammonium tetraphenylborate, tripropylammonium tetraphenylborate, tri(n-butyl)ammonium tetraphenylborate, tri(t-butyl) ammonium tetraphenylborate, N,N-dimethylanilinium tetraphenylborate, N,N-diethylanilinium tetraphenylborate, N,N-dimethylanilinium tetra-(3,5-bis(trifluoromethyl) phenyl)borate, N,N-dimethyl-(2,4,6-trimethylanilinium) tetraphenylborate, trimethylammonium tetrakis (pentafluorophenyl) borate, triethylammonium tetrakis (pentafluorophenyl) borate, tripropylammonium tetrakis (pentafluorophenyl)borate, tri(n-butyl)ammonium tetrakis (pentafluorophenyl)borate, tri(secbutyl)ammonium tetrakis (pentafluorophenyl)borate, N,N-dimethylanilinium tetrakis (pentafluorophenyl)borate, N,N-diethylanilinium tetrakis (pentafluorophenyl) borate, N,N-dimethyl-(2,4,6-trimethylanilinium) tetrakis(pentafluorophenyl) borate, trimethylammonium tetrakis-(2,3,4,6-tetrafluorophenylborate and N,N-dimethylanilinium tetrakis-(2,3,4,6-tetrafluorophenyl) borate; di-(i-propyl) ammonium tetrakis(pentafluorophenyl) borate, dicyclohexylammonium tetrakis(pentafluorophenyl) borate; triphenylphospnonium tetrakis(pentafluorophenyl) borate, tri(o-tolyl)phosphonium tetrakis(pentafluorophenyl) borate, tri(2, 6-dimethylphenyl)phosphonium tetrakis(pentafluorophenyl) borate; and N,N-dimethylanilinium tetrakis(3,5-bis (trifluoromethyl)phenyl)borate and combinations thereof.

21. The process of claim 12 wherein the at least one activator is present and is a combination of an ion forming activator and a group 13 reagent or a divalent metal reagent or alkali metal reagent.

22. The process of claim 12 wherein two or more of the olefin, diolefin or acetylenically unsaturated compounds are copolymerized.

* * * * *

UNITED STATES PATENT AND TRADEMARK OFFICE
CERTIFICATE OF CORRECTION

PATENT NO.     : 6,362,309 B1
DATED          : March 26, 2002
INVENTOR(S)    : Lund et al.

It is certified that error appears in the above-identified patent and that said Letters Patent is hereby corrected as shown below:

Column 19,
Line 31, the word "enylphospnonium" should be replaced with -- enylphosphonium --

Column 22,
Line 2, "1-norbomene," should be replaced with -- 1-norbornene --
Line 41, the word "enylphospnonium" should be replaced with -- enylphosphonium --

Signed and Sealed this

Eighteenth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,362,309 B1
DATED : March 26, 2002
INVENTOR(S) : Lund et al.

It is certified that error appears in the above-identified patent and that said Letters Patent is hereby corrected as shown below:

Title page,
Item [56], References Cited, please insert:
-- OTHER PUBLICATIONS
Japanese Abstract of 09255713 --.

Signed and Sealed this

Fifteenth Day of November, 2005

JON W. DUDAS
*Director of the United States Patent and Trademark Office*